(12) United States Patent
Szapiro et al.

(10) Patent No.: US 6,514,231 B1
(45) Date of Patent: Feb. 4, 2003

(54) DISPOSABLE SYRINGE WITH SINGLE VARIABLE VOLUME CHAMBER

(76) Inventors: Jaime Luis Szapiro, 1641 Tabare Street, Buenos Aires (AR); Leonardo Szames, 1641 Tabare Street, Buenos Aires (AR); Saul Moreno, 1641 Tabare Street, Buenos Aires (AR)

( * ) Notice: Subject to any disclaimer, the term of this patent is extended or adjusted under 35 U.S.C. 154(b) by 188 days.

(21) Appl. No.: 09/614,373

(22) Filed: Jul. 12, 2000

Related U.S. Application Data

(63) Continuation-in-part of application No. 09/344,974, filed on Jun. 28, 1999, now Pat. No. 6,149,628.

(30) Foreign Application Priority Data

Jul. 20, 1998 (AR) .......................................... 980103536
Jul. 14, 1999 (AR) .......................................... 990103437

(51) Int. Cl.⁷ ............................................. A61M 5/315
(52) U.S. Cl. .......................... 604/236; 604/89; 604/181; 604/218; 604/264
(58) Field of Search ................................ 604/236, 218, 604/265, 253, 264, 89, 181

(56) References Cited

U.S. PATENT DOCUMENTS

| 5,478,324 A | * | 12/1995 | Meyer ........................ 604/203 |
| 5,704,918 A | * | 1/1998 | Higashikawa ............... 604/191 |
| 5,785,683 A | | 7/1998 | Szapiro et al. ................ 604/89 |

* cited by examiner

*Primary Examiner*—Thomas Denion
*Assistant Examiner*—Ching Chang
(74) *Attorney, Agent, or Firm*—Bachman & LaPointe, P.C.

(57) ABSTRACT

A single chamber disposable syringe containing a medicament includes a valve member positioned in the variable volume chamber adjacent to the medicament outlet for selectively communicating the variable volume chamber with the medicament outlet.

5 Claims, 3 Drawing Sheets

A DISPOSABLE SYRINGE WITH SINGLE VARIABLE VOLUME CHAMBER

CROSS-REFERENCE TO RELATED APPLICATION

The instant application is a continuation-in-part of U.S. application Ser. No. 09/344,974 filed Jun. 28, 1999, now U.S. Pat. No. 6,149,628.

BACKGROUND OF THE INVENTION

The present invention is a single-chamber syringe having an internal valve-type closure actuatable by displacement of the plunger for administration of liquid products, especially medicinal products (medicament), which require the act of injection for administration thereof to a patient. More specifically, the present invention is drawn to a syringe belonging to the group which can be marketed with the product to be injected contained therein and are therefore known as disposable "prefilled syringes", and are provided with the medicinal product contained therein to ensure that the user does not come into contact with the product.

Numerous syringes are known which have been produced for the same purpose as stated above. All of them are formed of a cylindrical and hollow main body within which is accommodated the medicinal product which is to be administered and within which a coaxially arranged plunger moves. In all these cases, the lower base of the main cylindrical body is opened and allows the displacement of the plunger. In general, they include a flange which projects to the outside and is used as a support point for the user to push or pull on the plunger. At the other end, the opposite base of the main cylindrical body defines a hollow and coaxial tip which is frustoconical and acts as a connecting or coupling for the attachment of the injection needle. Such a device is shown in U.S. Pat. No. 5,785,683.

The novelty which distinguishes this embodiment lies in the fact that the syringe includes a very special valve-type closure for keeping the liquid content isolated, the closure being designed to open or close, allowing or preventing the passage of fluid to the injection needle by displacement of the plunger.

Co-pending application Ser. No. 09/344,974 relates to a syringe having a double internal chamber, which is suitable for bringing about the mixing of two separate components by displacement of the plunger. The valve used is internal, so that it requires no modification to the main cylindrical body of the syringe or even the incorporation of special plugs to close its open base, permitting the displacement of the plunger without undesirable losses of content occurring. The valve which is accommodated within the main cylindrical body, divides the latter into two internal chambers of variable volume, so that the active head of the plunger simultaneously acts as the face closing the distal chamber.

On the other hand, in the case of the present application, the valve is not used to form two internal chambers but is designed to act as an upper hermetic closing for a single isolated chamber which contains the product.

In the case of the '974 application, the novel internal valve uses two elastomeric portions which act by cooperating with one another, so that they mix the originally isolated components, when the plunger moves in a direction opposite to the injection action and allows the mixture to escape toward the injection needle when the plunger is displaced, performing the injection action.

SUMMARY OF THE INVENTION

The internal valve-type plug incorporated in the single-chamber syringe according to the present invention, is characterized in that it is arranged adjacent to the connecting cone of the syringe bearing on the internal face of its upper base, so that the projecting portion that it possesses, in this case, blocks communication with the injection needle, while the lower base of the internal body of the plug is the upper base of the internal chamber of the syringe which accommodates the liquid.

In this manner, when the user displaces the plunger, by pulling in the direction opposite to the injection direction, the internal body moves away from the periphery, opening communication to the needle. Once this communication has come about, the conventional method is followed of displacing said plunger in the injection action whereby the liquid flows toward the needle and, through the needle, to the outside, passing through the valve assembly.

An advantage over the known art lies in the fact that it is no longer necessary to include a plug in the connecting cone within which communication with the injection needle is established, since the valve plug itself produces hermetic sealing from the interior of the syringe.

BRIEF DESCRIPTION OF THE DRAWINGS

In order to facilitate understanding of the design and functional features of the inventive single-chamber syringe, a description is given below of a preferred embodiment, which is illustrated schematically wherein.

DETAILED DESCRIPTION

Figure 1:
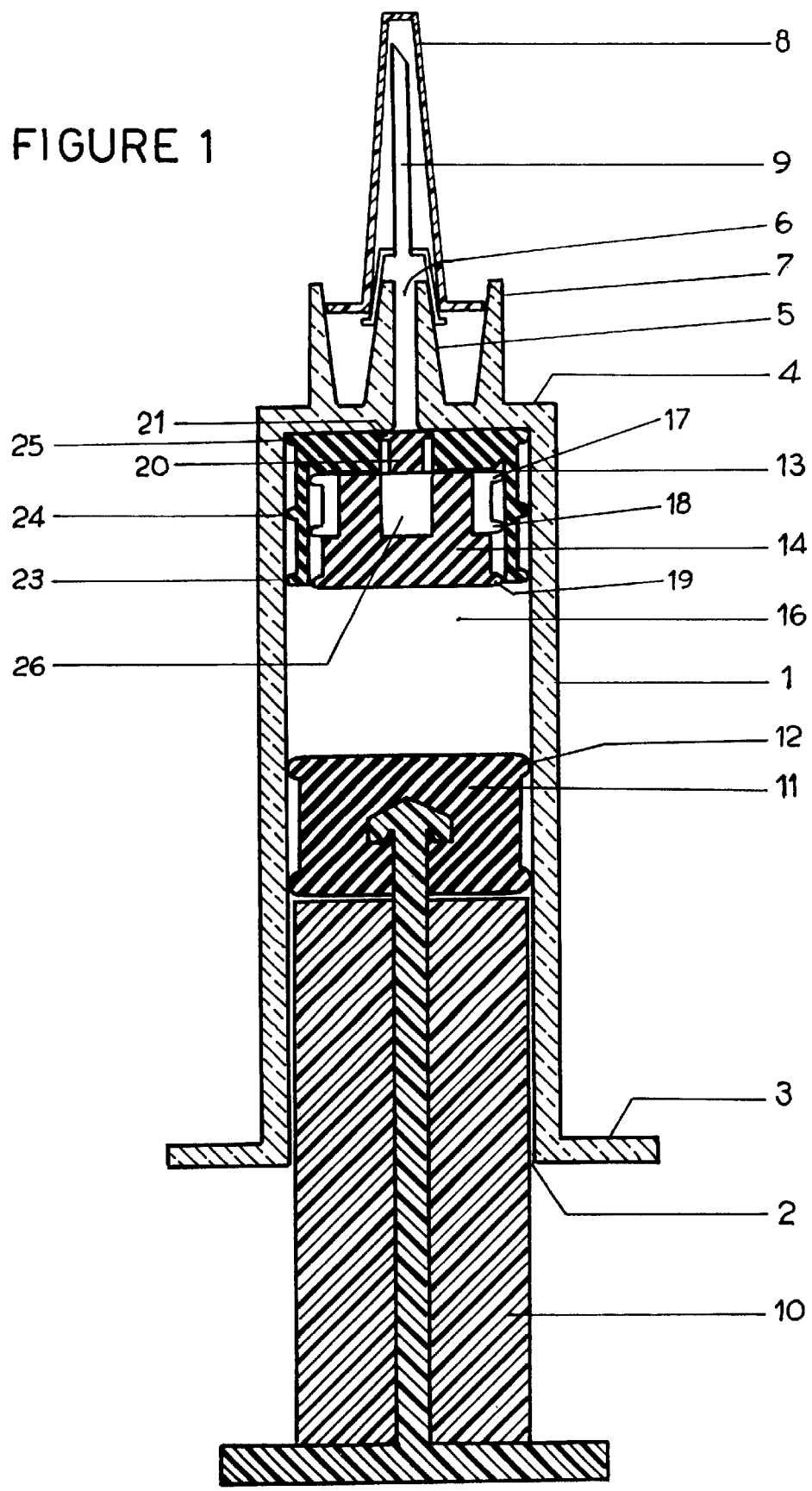
FIG. 1 is a sectional view in a longitudinal vertical plane which shows a needle of the prefilled type having a valve means as protected by the present patent and arranged in the closed position.

It should be made clear that, in all the figures, the same reference numerals correspond to the same or equivalent constituent parts or elements of the assembly, in accordance with the example selected for the present explanation of the single-chamber syringe forming the subject of the invention.

As may be appreciated from the drawings, the single-chamber syringe having an internal valve-type closure to which the present patent relates belongs to the type of those comprising a main body (1), which is a circular cylinder of straight axis, having its lower base (2) completely open, in which is also included the annular flange (3) which the user uses as a support for actuating the plunger (10).

The upper base (4) includes the coaxial hollow injection tip (5), where an internal tube (6) is defined through which the liquid flows toward the injection needle (9) protected by the sheath (8) which is retained removably when inserted, with a close fit, into the annular cavity defined by the face (7).

As is apparent from these three figures, the plunger (10) possesses an active head (11) which acts as a sliding closure plug to prevent the escape of liquid from the interior of the main cylindrical body (1). This is an elastomeric element whose annular flange (12) bears with friction on the cylindrical surface of the body (1), providing a seal to said closure to ensure that no undesirable leaks of liquid take place without obstructing the normal displacement of the plunger.

As can be seen in FIG. 1, the internal valve assembly used by the syringe according to the invention comprises a peripheral body (13) which acts to cooperate with an internal body (14), which assembly is arranged adjacent to the upper base of the main body and within the latter, so that a single internal chamber (16) is defined between this valve assembly and the active head (11) of the plunger and is designed to accommodate and keep isolated the liquid product contained therein.

The special design of this valve assembly enables the displacements of said plunger to bring about the opening and closure of the passage to the needle. This is done by means of the suction and pressure exerted by the liquid content itself when said displacements of the plunger take place.

From a study of the three representative figures, it is possible to understand the special design of this valve assembly and, in particular, how it acts in a single-chamber syringe.

The internal valve body (14) possesses a special projecting central section (21) which, being arranged coaxially with said tube (6) communicating with the injection needle (9), acts as an upper closing plug ensuring the proper isolation of the latter from the chamber (16).

Since this is a valve means where relative and combined movements take place, both the body (13) and the body (14) and its projecting section (21) possess respective annular flanges indicated by references (17, 18, 19, 20, 23, 24 and 25), which bear upon corresponding internal cylindrical surfaces upon which they move.

FIG. 1 shows the arrangement of all the elements and parts that intervene when the syringe is in the position of rest, containing the liquid medicinal product in said chamber (16). The seal is absolutely leaktight and secure both toward the lower base and toward the upper base of said syringe.

Figure 2:
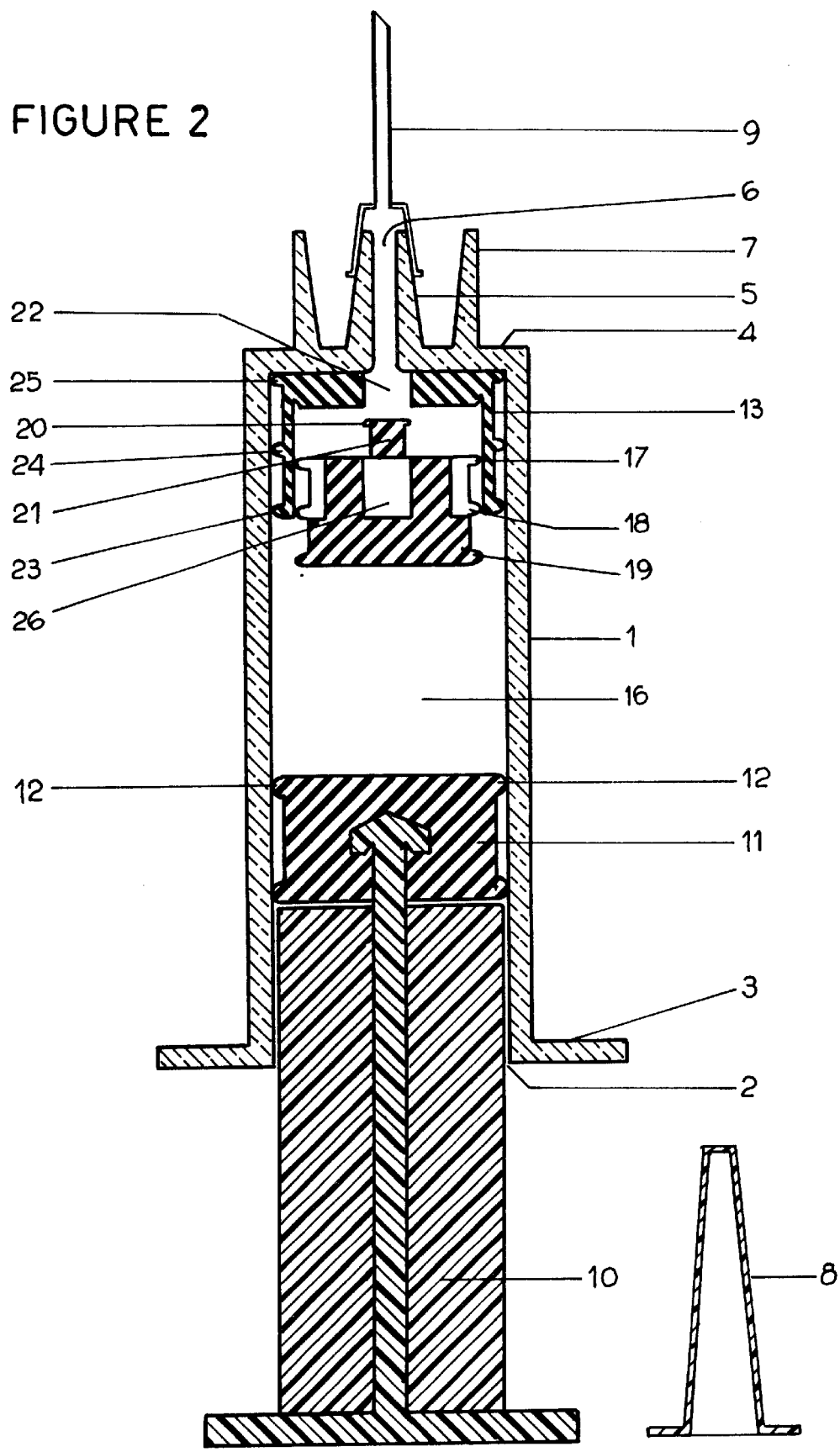
FIG. 2 is a sectional view similar to the previous figure but, in this case, with the same valve means in the position adopted when the user displaces the plunger in the direction opposite to the injection direction.

From a study of FIG. 2, it will be understood that when the plunger (10) is moved in the direction opposite to that of injection, a vacuum is created in said chamber (16) which produces the relative movement of the body (14) relative to the peripheral body (13), so that an upper communication tube (22) is opened with said tube (6) which faces the injection needle.

As is apparent from the three figures, this tube (22) is no more than an opening or orifice made in the upper base of the peripheral body (13), coaxial with the axis of symmetry of the syringe and therefore aligned with said tube (6) of the tip (5) through which the liquid circulates.

Figure 3:
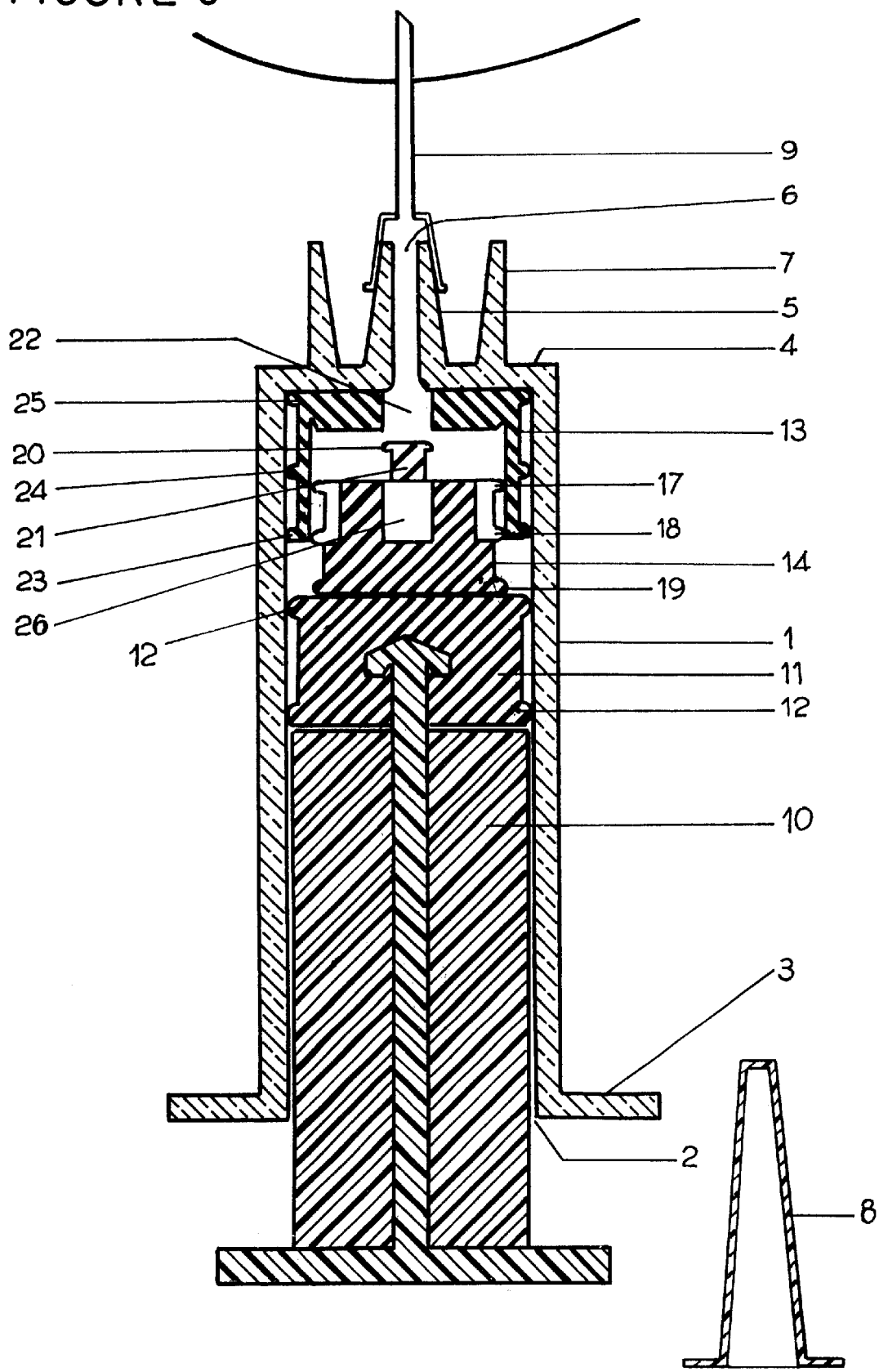
FIG. 3 is the same view in longitudinal section, but in this case showing the arrangement of the elements taking part in the course of the injection action.

From a study of FIG. 3, it will be understood that when said plunger (10) moves in the injection action, the fluid advances in the direction opposite to that shown in the previous figure, passing first through the transfer cavities (26) and then, through said tube (22) progressing toward the needle (9).

When the active head of said plunger (10) enters into contact with the body (14), it can continue advancing and therefore dislodging liquid toward the tube (22) until the projecting and coaxial section (21) itself prevents it.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A single chamber disposable syringe containing a medicament comprises:

a main body having a sidewall, an upper base having a medicament outlet and a lower base having an opening which receives a movable plunger, said sidewall, upper base and plunger together define a variable volume chamber; and a valve member positioned in said variable volume chamber adjacent to said upper base for selectively communicating said variable volume chamber with said medicament outlet when said plunger is moved alternately away from and toward said upper base, wherein said valve member comprises (1) a hollow peripheral valve portion sealingly located on the sidewall of the chamber and abutting said upper base and (2) a rigid inner valve portion movably received in the hollow peripheral valve portion and moveable between a first position for establishing communication between the variable volume chamber and said medicament outlet and a second position for prohibiting communication between said variable volume chamber and said medicament outlet, wherein movement of the plunger in a first direction away from said upper base moves the inner rigid valve portion to the first position for communicating the variable volume chamber with said medicament outlet and movement of the plunger in a second direction tranfers the medicament from the variable volume chamber to said medicament outlet until the plunger abuts the inner rigid valve portion and moves same to the second position.

2. A syringe according to claim 1, wherein the hollow valve portion is cup-shaped and has a sidewall portion extending from a base portion, the base portion includes a control conduit.

3. A syringe according to claim 2, wherein the inner rigid valve portion has a body portion sealingly received on the sidewall portion on the hollow valve portion and a projecting portion received in the central conduit of the hollow valve portion when in the second position.

4. A syringe according to claim 1, wherein the hollow peripheral valve portion has a plurality of flanges for sealing on the sidewall of the chamber.

5. A syringe according to claim 4, wherein the body portion has a plurality of flanges for sealing on the sidewall portion of the hollow peripheral valve portion.

* * * * *